United States Patent
Menon et al.

(10) Patent No.: US 11,052,239 B2
(45) Date of Patent: Jul. 6, 2021

(54) CANNULA, CANNULA SYSTEM, HEART PUMP SYSTEM AND METHOD FOR RELIEVING THE VOLUME OF A HEART

(71) Applicant: Berlin Heart GmbH, Berlin (DE)

(72) Inventors: Ares K. Menon, Berlin (DE); Franziska Gräbner, Berlin (DE)

(73) Assignee: Berlin Heart GmbH, Berlin (DE)

( * ) Notice: Subject to any disclaimer, the term of this patent is extended or adjusted under 35 U.S.C. 154(b) by 0 days.

(21) Appl. No.: 16/342,342

(22) PCT Filed: Oct. 20, 2017

(86) PCT No.: PCT/EP2017/076811
§ 371 (c)(1),
(2) Date: Apr. 16, 2019

(87) PCT Pub. No.: WO2018/073399
PCT Pub. Date: Apr. 26, 2018

(65) Prior Publication Data
US 2019/0255234 A1    Aug. 22, 2019

(30) Foreign Application Priority Data
Oct. 20, 2016 (EP) .................................... 16194899

(51) Int. Cl.
*A61M 60/857* (2021.01)
*A61B 17/34* (2006.01)

(52) U.S. Cl.
CPC ....... *A61M 60/857* (2021.01); *A61B 17/3415* (2013.01); *A61M 2205/3344* (2013.01)

(58) Field of Classification Search
None
See application file for complete search history.

(56) References Cited

U.S. PATENT DOCUMENTS

| | | | |
|---|---|---|---|
| 3,995,617 A | | 12/1976 | Watkins et al. |
| 5,190,528 A | * | 3/1993 | Fonger .................. A61M 25/01 477/63 |
| 2014/0012066 A1 | * | 1/2014 | Aboul-Hosn ....... A61M 1/3613 600/16 |

(Continued)

FOREIGN PATENT DOCUMENTS

| CA | 968101 | 5/1975 |
|---|---|---|
| DE | 2143628 | 4/1973 |

(Continued)

OTHER PUBLICATIONS

International Search Report with English translation, dated Jan. 12, 2018, pp. 1-6, issued in PCT/EP2017/076811, European Patent Office, Rijswijk, The Netherlands.

*Primary Examiner* — Ankit D Tejani
(74) *Attorney, Agent, or Firm* — Brinks Gilson & Lione

(57) ABSTRACT

A cannula for relieving the left side of the heart is provided, the cannula having a cannula shaft comprising a heart-side inlet and a pump-side outlet. A lumen extends between the inlet and the outlet, and a suture ring for connecting the cannula to a left atrium is arranged on an outer side of the cannula shaft. The outlet is configured such that the outlet can be connected to a pump and the length of the cannula shaft between the suture ring and the outlet is such that the cannula shaft can be guided outwards through an intercostal space.

15 Claims, 11 Drawing Sheets

(56) References Cited

U.S. PATENT DOCUMENTS

| | | | | |
|---|---|---|---|---|
| 2014/0364880 A1* | 12/2014 | Farnan | .................... | A61B 17/11 |
| | | | | 606/151 |
| 2015/0066139 A1* | 3/2015 | Van Bladel | ........... | A61F 2/2487 |
| | | | | 623/2.11 |
| 2015/0224240 A1* | 8/2015 | Farnan | ................ | A61M 1/3653 |
| | | | | 600/16 |
| 2016/0022896 A1* | 1/2016 | Burkhoff | ............. | A61M 1/3667 |
| | | | | 600/17 |
| 2016/0101230 A1* | 4/2016 | Ochsner | ............... | A61B 5/1073 |
| | | | | 600/17 |
| 2016/0206795 A1* | 7/2016 | Reichenbach | ...... | A61M 25/005 |

FOREIGN PATENT DOCUMENTS

| | | |
|---|---|---|
| EP | 0 092 927 | 11/1983 |
| WO | WO 2004/082742 A1 | 9/2004 |
| WO | WO 2014/137511 A1 | 9/2014 |
| WO | WO 2016/032647 A1 | 3/2016 |

\* cited by examiner

CANNULA, CANNULA SYSTEM, HEART PUMP SYSTEM AND METHOD FOR RELIEVING THE VOLUME OF A HEART

CROSS-REFERENCE TO RELATED APPLICATIONS

This application is a 371 nationalization of international patent application PCT/EP2017/076811 filed Oct. 20, 2017, which claims priority under 35 USC § 119 to European patent application 16 194 899.7 filed Oct. 20, 2016. The entire contents of each of the above-identified applications are hereby incorporated by reference.

TECHNICAL FIELD

The subject matter of the present application is a cannula for relieving the heart, a cannula system that comprises such a cannula and an obturator or a trocar, a heart pump system that comprises a heart pump and two cannulas, and furthermore a method for relieving the volume of a heart.

DETAILED DESCRIPTION

Figure 1:
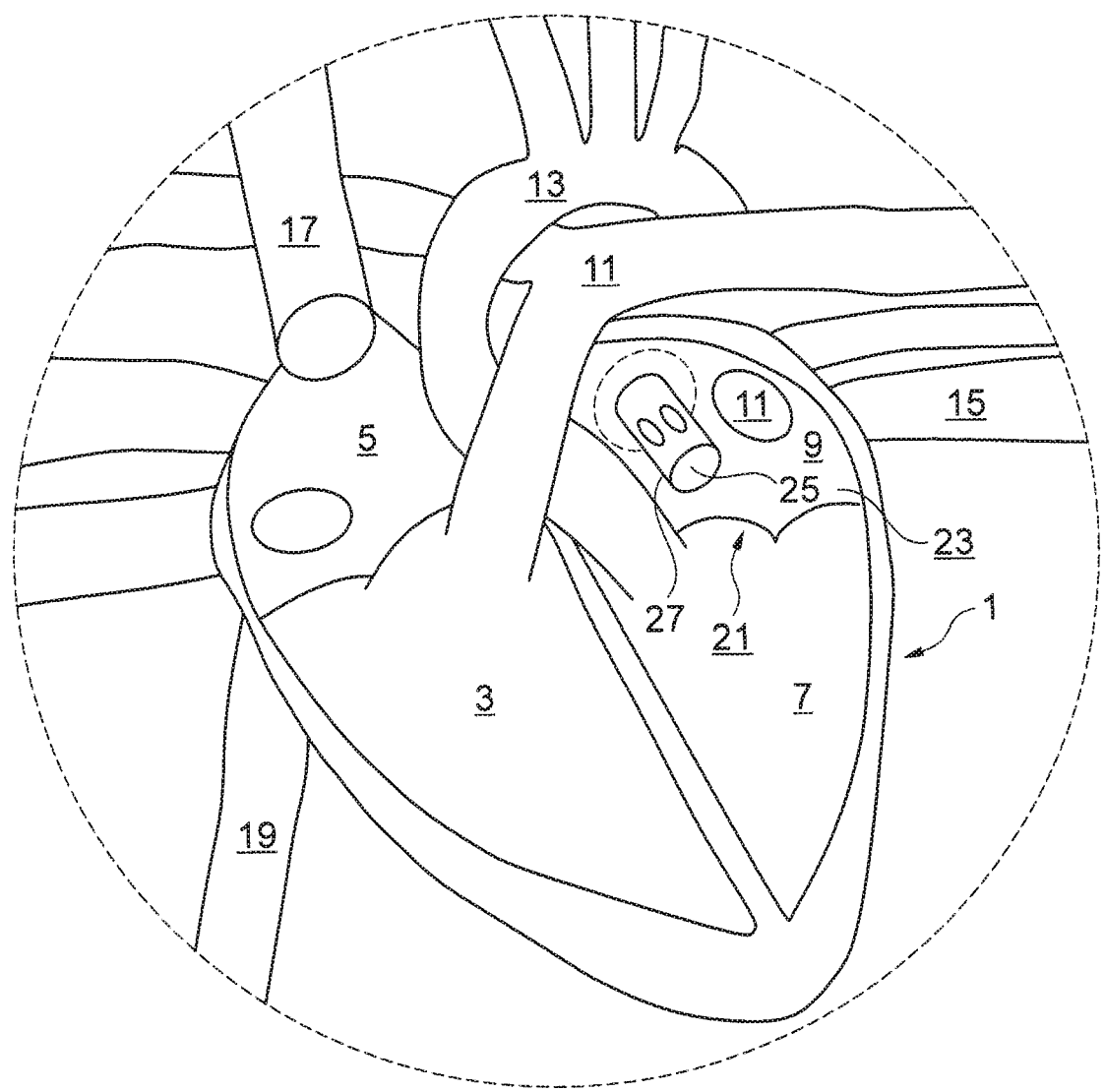
FIG. 1 is a schematic view of a ventral section through a heart.

When there is acute left heart failure following myocardial infarction, decompensation of a cardiac insufficiency, or other pathologies affecting left heart function with decompensation, the left ventricle develops a pumping weakness that has, inter alia, three effects. First, the body's circulation is undersupplied with oxygen and nutrient-rich blood, the tissue is oversaturated (acidosis), and organ failure threatens. Second, the left ventricle dilates with increased volume and pressure load. Third, blood backs up in the pulmonary circulation system, with increased pulmonary capillary pressure and pulmonary hypertension and the threat of pulmonary edema.

When left heart failure occurs, frequently intra-aortal balloon pumps (IABP) are used, but extracorporeal heart support systems for extracorporeal membrane oxygenation (ECMO) is often used as well. Access to large body vessels is generally provided via inguinal vessels. Adequate circulation in the patient may be assured within a few minutes in this manner. An oxygenator for improving oxygen supply is frequently inserted in series, since acute left heart failure frequently involves pulmonary congestion with pulmonary edema. However, in left heart failure, the inadequate pumping by the left ventricle is causal—poor oxygenation is only secondary.

Nevertheless, use of the ECMO has become commonplace in patient cohorts with primary left heart failure because ECMO restores marginal or deficient circulation rapidly and effectively. The term extracorporeal life support (ECLS) was therefore introduced to differentiate these patient cohorts from the purely ECMO pulmonary failure cohort. In ECLS, a large vein is selected as the inflow to the pump or to the oxygenator and a large artery is selected as the inflow of blood into the body's circulatory system. Based on this cannulization technique, there is no direct volume relief of the severely contracted left ventricle. Thus eventual recovery of left ventricular contractility is hardly possible.

Other described methods for relieving the left ventricle, e.g. via the left atrium by means of a catheter or an atrioseptectomy, may not attain efficient relief of the left ventricular cavum. Therefore, the prospect for a patient's left ventricular contractility to recover solely using ECLS is remote.

So-called "left-ventricular assist devices" provide an effective option, however. These devices are more complex in terms of implantation, however, and cost much more than the aforesaid ECMO, IABP, and ECLS pump systems.

The present invention is intended to provide an efficient, cost-optimized system for rapid use and safe implantation in the heart, so that the contractility of the left ventricle may be improved.

The object is attained using the cannulas, the cannula system, and the heart support system described herein. A method for relieving volume in the left side of the heart is furthermore described.

In a first embodiment, the cannula for relieving the left side of the heart comprises a cannula shaft having a heart-side inlet and a pump-side outlet. Extending between the inlet and the outlet is a lumen through which the blood from the left side of the heart, preferably the atrium or the ventricle, may be conducted out of the body. The outlet is configured such that it may be connected to a pump.

A suture ring, with which the cannula may be attached to a wall of the left atrium, is attached to an exterior of the cannula shaft. To this end, a minimally-invasive right-side thoracotomy with subsequent incision of the pericardium may be performed, for example, wherein the left atrium is exposed and retraction sutures are placed on the cardiac wall and then pulled through the suture ring.

In this embodiment, the cannula has a wall thickness along the cannula shaft that permits a dimensionally stable lumen. This means that relatively high forces have to be applied to clamp the lumen, and the pressures prevailing in the blood flow are not adequate to collapse the lumen. For example, the wall thickness may be between 1 and 4 mm, the wall thickness also being selectable as a function of material.

As already stated in the foregoing, the cannula is embodied such that it may be guided outward from the left atrium through an intercostal space on a right side (as seen from an anterior view) of the patient (in other exemplary embodiments, the cannula may be embodied on the other, left side). Such a length ensures that, once the cannula has been connected to a heart pump, the patient does not have to remain in bed because no cannula outlet is conducted through the femoral artery. The patient regains his mobility more rapidly because of this, such that the recovery process is better supported.

As already mentioned in the foregoing, in order to implant a cannula according to the application, the left atrium is exposed by means of a minimally invasive right thoracotomy and pericardial retraction sutures are placed. The cannula is initially provided, for example, with a trocar that blocks the lumen of the cannula. For example, following administration of heparin, the atrial wall is punctured using the Seldinger technique and then a guide wire is advanced, a trocar being inserted along it and the cannula being advanced into the left atrium or left ventricle via the trocar. The trocar may be used, for example, to puncture the atrial wall, and the cannula is inserted into the atrium through the opening made by means of the trocar. In this way the cannula may be implanted in the so-called "off-pump" mode, i.e., the outlet of the cannula is not connected to a pump outside of the body until the cannula has been implanted. Then the cannula suture ring is joined to the wall of the left atrium such that the cannula is positioned securely against the wall of the heart; because the cannula is preferably guided through an intercostal space, however, only minor forces act on the wall of the atrium. Then the outlet of the cannula is connected to the inlet of an extracorporeal heart pump or to a VAD.

In one embodiment of the cannula, the latter has a cannula shaft having a length of more than 20 cm, preferably more than 30 cm. In this way it is assured that the cannula may project far enough out of the rib cage that the there is no problem connecting an extracorporeal heart pump and patient mobility is assured.

In another embodiment, the cannula shaft has a wall thickness of 2 to 4 mm. Such a wall thickness assures that the cannula or the lumen of the cannula does not collapse under the pressures prevailing in the blood flow and that its cross-section does not markedly decrease. This assures a more stable flow of blood through the cannula.

In another embodiment, the cannula shaft is produced from a biocompatible material, such as silicone, for instance. Biocompatible materials are preferably suitable for temporary implantation and subsequent explantation as soon as the patient no longer requires an external heart support or as soon as it is apparent that the patient will require a permanent LVAD. The exterior of the cannula shaft is preferably smooth, such that it will not easily grow into the tissue. This assures that even after several weeks of implantation the cannula will be able to be explanted with no problem. A wall thickness between 1 an 5 mm may be selected for the wall thickness of a cannula made of silicone so that the lumen of the catheter may also be held between the ribs such that it is dimensionally stable.

In another embodiment, the cannula comprises a pressure sensing line with a pressure inlet and a pressure outlet, the pressure inlet of the pressure sensing line being arranged on the heart side of the suture ring. This means that the pressure inlet is essentially arranged between the suture ring and the (cannula) inlet. The cross-section of the pressure sensing line is smaller than the cross-section of the cannula lumen. The cross-section of the pressure sensing line is preferably at least ten times smaller than the cross-section of the cannula lumen. In this way it is assured that the pressure sensing line does not significantly increase the diameter of the cannula. By means of the pressure sensing line it is possible to monitor the pressure inside the left atrium continuously without having to insert a separate pressure sensing line into the cannula temporarily via a port, for instance.

The pressure sensing line is preferably guided along an exterior of the cannula shaft. The pressure sensing line may be welded or glued to the exterior of the cannula shaft, for example.

In another special embodiment, the pressure sensing line is guided in the lumen of the cannula.

In another special embodiment, the pressure sensing line is arranged as a separate lumen in the cannula shaft wall.

The pressure sensing line is configured such that it may be connected to an external pressure measuring system, for instance a conventional blood pressure measuring system such as the intensive monitors from Philips, HP, or Siemens. The pressure outlet is equipped with an adapter, for instance, that is standardized and may be coupled to the selected system. Although in numerous embodiments the pressure sensing line is connected to the exterior of the cannula shaft in a material fit, the outlet side of the pressure sensing line may project beyond the outlet of the cannula and be significantly longer than the cannula shaft so that it is possible to couple it to an external pressure measuring system.

Alternatively or in combination with the pressure sensing line, a pressure sensor, such as for example a mechanical-electromagnetic sensor, may be arranged in the vicinity of the inlet of the cannula. A pressure sensor provided with a membrane may also be arranged at the cannula inlet.

In another embodiment, the inlet comprises at least one drain element. A drain element shall be understood to mean a number of openings that are arranged circumferentially around the wall of the cannula shaft in the vicinity of the inlet. This term shall also include a single opening added there. The drain element, which may comprise, for example, two, three, four or more openings, assures that blood can be drawn not only solely through the inlet, but also essentially perpendicular thereto into the lumen of the cannula shaft through the holes of the drain element. In this way it is possible to prevent significant dead volumes in the atrium and the risk of thrombus formation is reduced. In addition, flow properties within the atrium and when drawing in the blood are improved.

In another embodiment, at least two drain elements spaced apart from one another are arranged between the suture ring and the inlet.

In another embodiment, a first drain element may be arranged such that it is arranged in the left atrium, while the second drain element and the inlet may project through the mitral valve into the left ventricle and take in blood here. Particularly good volume relief of the left atrium and left ventricle is attained by means of a plurality of drain elements arranged in a different parts of the left heart. The cannula shaft is embodied such that, between the suture ring and the inlet, the cannula shaft is long enough that the inlet projects through the left atrium into the left ventricle.

In another embodiment, between the suture ring and the inlet the cannula comprises a contrasting material, such as, for example, an X-ray contrasting material, such as, for example, a metal, or a material that provides a contrast for echocardiography. In this way, the positions of the inlet and suture ring in the patient's circulatory system may be monitored by means of an X-ray device or echocardiogram during minimally invasive implantation.

Furthermore, the cannula may be part of a cannula system that comprises, in addition to the cannula, an obturator or a trocar. The trocar and/or obturator is embodied such that they completely block the cannula lumen. A trocar shall be understood to be a device that may be used to puncture the atrial wall or to enlarge an existing puncture in the atrial wall during a procedure using the Seldinger technique. An obturator does not have a tip like this, but instead is used solely for blocking the lumen so that the cannula may be implanted and explanted. In this case, the atrial wall is punctured by means of other methods.

A cannula described in this application that has, in addition to the cannula, an extracorporeal heart pump or a VAD, and another cannula, is preferably used in a heart pump system. The extracorporeal heart pump may be any heart pump approved for providing a blood supply to a patient in an extracorporeal manner. The outlet of the cannula described here is connected to the inlet of the pump, and the outlet of the pump may be connected, via an oxygenator or without the presence of an oxygenator, to the inlet of the other cannula. The other cannula is designed such that it may be connected, for example, to a subclavian artery or inguinal artery. Connecting to a subclavian artery is preferred, since this way the patient's mobility is less restricted and thus further improvement of the patient's condition may be attained.

In a method for implantation or for relieving volume of the left side of the heart, in a few embodiments the cannula is inserted between two ribs into the intercostal space, and prior to starting up the pump a spacer is arranged between the ribs so that if the patient moves, the ribs moving towards one another cannot pinch off the cannula disposed therebetween, causing the supply of blood to the patient to be too low.

Additional details and embodiments are described in greater detail using the figures in the following.

FIG. 1 depicts a ventral section of a human heart 1. The right ventricle 3, right atrium 5, left ventricle 7, and left atrium 9 are visible. Also visible are the pulmonary artery 11, aorta 13, pulmonary veins 15, and the superior vena cava 17 and inferior vena cava 19. The left atrium 9 receives blood from the pulmonary veins 15. Normally the blood flows through the mitral valve 21 into the left ventricle 7 and from there through the aorta 13 into the body. In the case of left heart insufficiency, the pumping performance of the left ventricle 7 is no longer sufficient for supplying enough blood to the body. Because of this, the present application suggests guiding a cannula through the posterior atrial wall 23, as is illustrated in FIG. 1 by the inlet 25 of a sketched-in cannula 27. A closer description of the details of such a cannula shall be provided in the subsequent figures.

Figure 2:
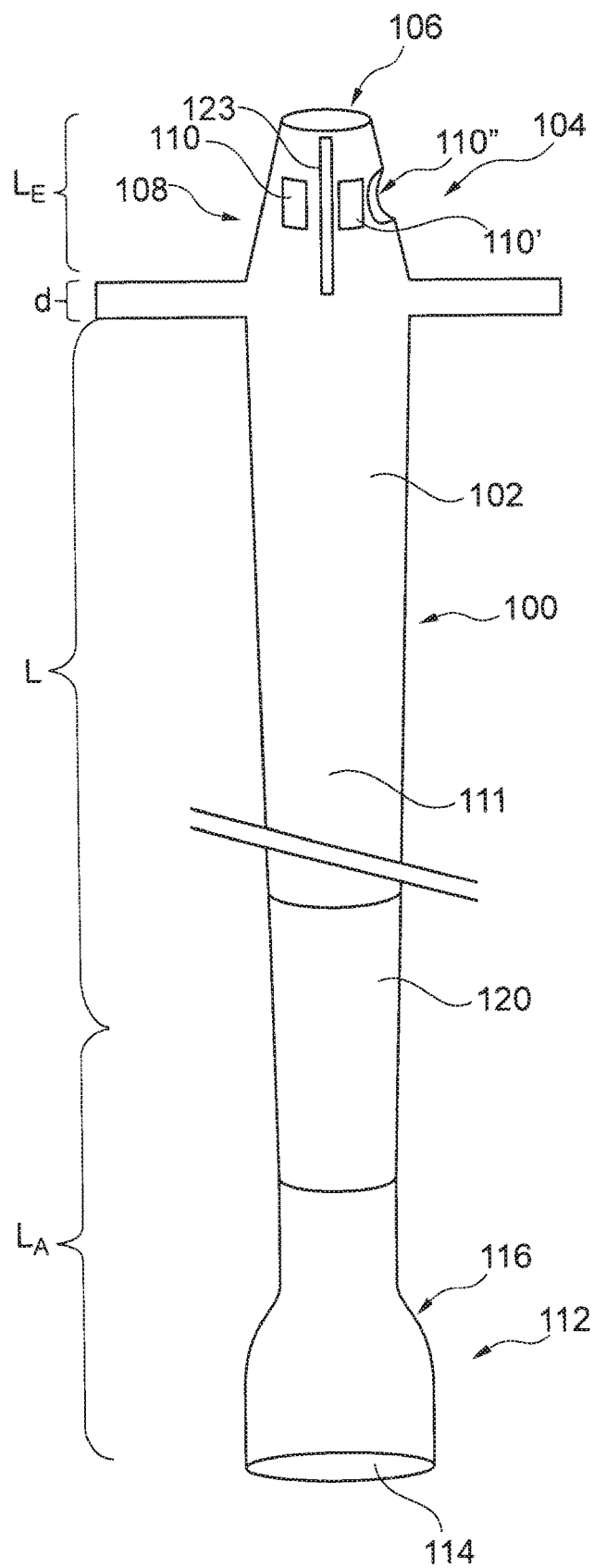
FIG. 2 depicts one embodiment of a cannula.

FIG. 2 depicts an exemplary cannula 100. The cannula comprises a cannula shaft 102 that may comprise silicone, for example. Silicone has the advantage that it is a biocompatible material and is not rejected by the human body. Other biocompatible plastics may also be used as the material or material combination, however. Exemplary materials are polyurethane. The surface of the cannula shaft 102 is preferably not very rough, i.e. preferably does not have any structuring of the outer wall of the cannula shaft, so that it is prevented from growing into the tissue through which the cannula shaft is guided. In the following, the terms "distal" and "proximal" shall be added for orienting individual components of the cannula. "Distal" indicates an orientation away from the surgeon and "proximal" an orientation towards the surgeon.

An inlet 104 is disposed at the distal end of the cannula shaft 102. The inlet 104 comprises a distal opening 106 as well as a drain element 108 with drain openings 110, 100', and 110". The inlet is configured such that it is or may be positioned in the left atrium. This means that the cannula may be produced in different sizes in order to be connected to hearts of different sizes. Blood may be drawn through the distal opening 106 into a lumen 111 of the cannula shaft 102.

An outlet 112 having a proximal opening 114 is disposed at the proximal end of the cannula shaft. The outlet 112 comprises a widened region 116 that has a diameter wider than a majority of the rest of the cannula shaft 102. This widened region 116 may be widened, for example, in order to be able to produce a connection to a pump of a heart pump system. In other embodiments of a cannula, the latter may have an adapter at the outlet for connecting to a pump. These adapters may be standardized and may have a diameter of ⅜" or ½", for example.

A synthetic web 120 that promotes growing into a body tissues is arranged on a limited segment of the cannula shaft 102. For example, the web may be a felt that comprises a biocompatible material. This web is preferably arranged in a region of the cannula shaft 102 in which the cannula 100 passes through the skin of a patient. The risk of infection for a patient is reduced due to the web 120 growing into the body tissue in the region where the cannula passes through the skin.

Furthermore, disposed in the vicinity of the inlet 104 is a suture ring 122 that preferably goes completely around the cannula shaft 102. This suture ring has a wider diameter than the lumen 111 and is used to join the cannula to the exterior of the posterior atrial wall. The suture ring may consist of or comprise silicone, for example, but preferably includes a textile material that can be sutured, because the latter may be sutured to the atrial wall in a simple manner. Since the suture ring remains on the exterior of the atrium, only the inlet 104 is disposed in the atrium as soon as the cannula has been sutured to the heart. The length $L_E$ of the inlet along a longitudinal axis of the cannula shaft is between 0.5 and 3 cm, depending on the embodiment. The thickness d of the suture ring along the longitudinal axis of the cannula is preferably less than 1 mm, and is maximally 0.5 cm. The cannula extends across a length L between the suture ring and the web 120. This length L is preferably at least 20 or 30 cm or longer. The length L should be designed such that the cannula may be guided outward from the atrial wall through an intercostal space and enough length $L_A$ remains outside of the body for the cannula to be connected to a heart pump system and the length $L_A$ permits sufficient patient mobility. In some embodiments, lengths $L_A$ are more than 30 cm, for example between 20 and 140 cm, preferably between 20 and 110 cm. The length $L_A$ may also be selected such that a patient may carry the extracorporeal blood pump in a pocket on his body. A majority of the length $L_A$ that connects to the web may remain outside of the body, for example the length $L_A$ may be a length between 20 and 80 cm. Thus the total length $L_E$, L, and $L_A$ may be between 50 cm and 180 cm, depending on the height and age of the patient.

As mentioned in the foregoing, the inlet 104 comprises a distal opening 106 and a drain element 108. The drain element 108 is designed such that it improves the flow within the lumen 111. The distal opening 106 may have, for example, a diameter transverse to the longitudinal axis of the cannula of 0.3 cm to 3 cm, preferably 0.5 cm to 1.5 cm. The distal opening 106 may have a round or oval area and is preferably spaced apart from a distal end of a drain element opening 110, for example between 0.2 cm and 1 cm. The size of a drain element opening 110 may be 25 $mm^2$, for example, but may be larger or smaller. Overall a drain element 108 may have more than one drain element opening 110, preferably two or more drain element openings, particularly preferably four or more drain element openings. In some embodiments, the drain element openings are smaller than the distal opening and are disposed proximal thereto. However, all of the drain element openings are disposed distal to the suture ring, so that they are also all disposed in the atrium when the cannula is implanted.

The inlet 104 furthermore comprises a contrasting strip 123 that is made of, for example, a metal and to which silicone material of the inlet is added. While the cannula is being implanted, it is possible, for example, to use the contrasting strip and fluorescence spectroscopy to monitor whether the cannula is disposed in the desired location in the atrium.

Figure 3:
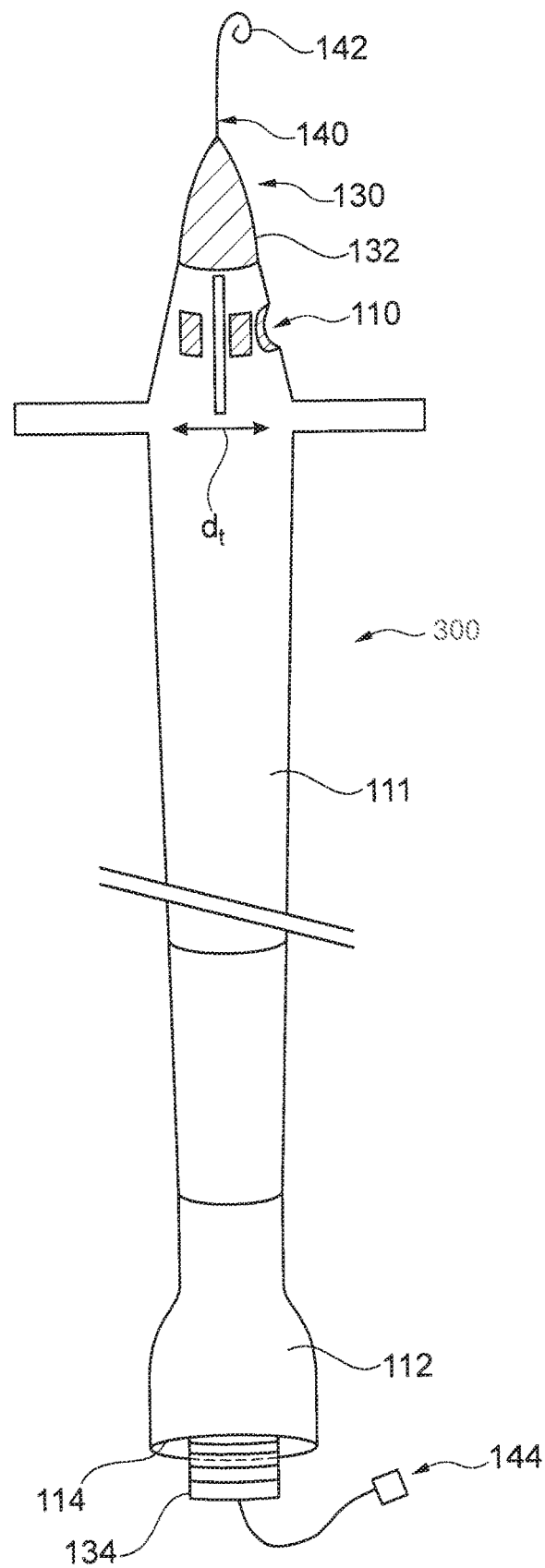
FIG. 3 depicts another view of the cannula from FIG. 2.

FIG. 3 depicts the cannula 100 in combination with a trocar 130. The trocar 130 is inserted into the lumen 111 and closes or blocks the latter. The trocar is longer than the cannula and thus extends beyond the distal opening 106 and beyond the proximal opening 114. During implantation, the trocar guides the cannula to and into the atrial wall. The trocar 130 closes the lumen such that no fluid can penetrate through the drain element openings 110 to the outlet, either, for as long as the trocar is inserted into the lumen 111. It may also be seen in the figure that the trocar has a pointed shape pointing in the direction of its distal end 132, in this case is conically pointed, so that the tip is suitable for puncturing the atrial wall. The opening added by the trocar is further widened by means of the exemplary conical shape, so that the inlet of the cannula or the distal end of the inlet (which essentially has a similar diameter or circumference as the trocar in the region of the inlet) may also be inserted into the atrium.

Figure 3A:
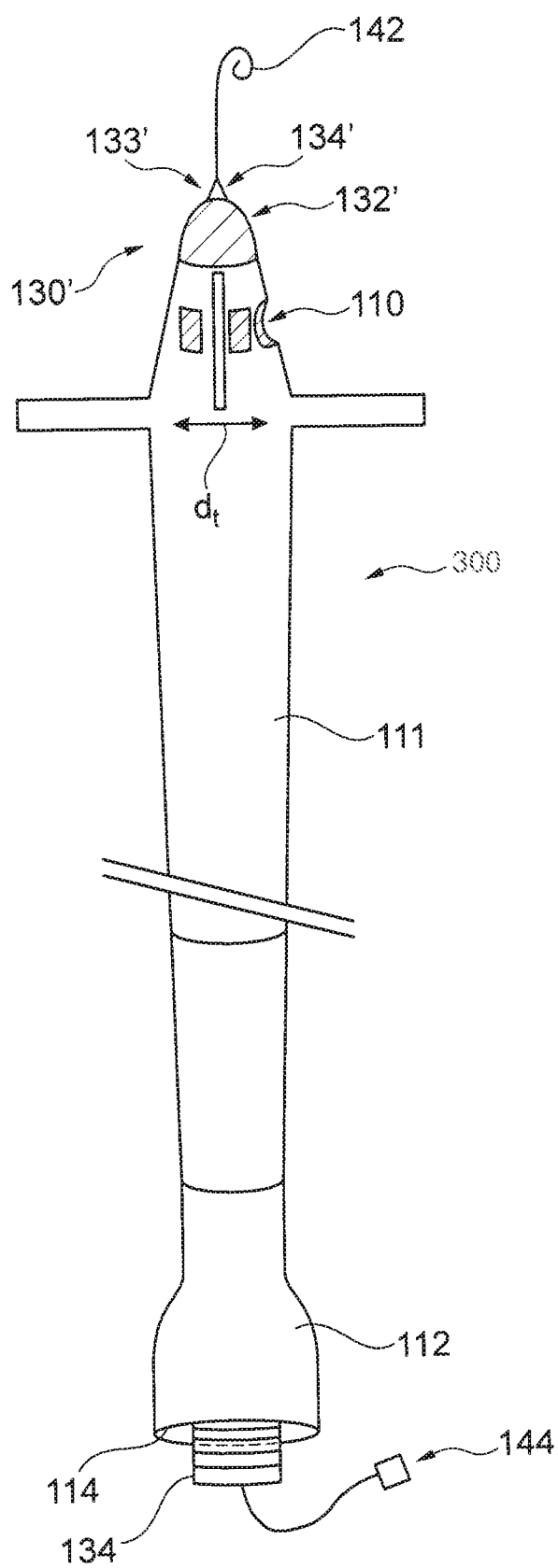
FIG. 3A depicts an embodiment from FIG. 3 having an alternative trocar.

FIG. 3A depicts the embodiment of the cannula 100 in FIG. 3 with an alternative trocar. The distal end 132' of the trocar 130' is essentially round, a puncturing tip 134' being arranged at the most distal region 133' of the distal end 132'. The puncturing tip may be configured to be in a conical or cross-slot shape, or may be configured to have only one cutting surface.

The cannula may be inserted, for example, with the Seldinger technique. To this end, a guidewire 140 is advanced through the intercostal space between two ribs up to the posterior atrial wall. The distal end 142 of the guidewire is employed, inter alia, to puncture the heart. Then the distal end 132 of the trocar 130 is threaded onto the proximal end 144 of the guidewire (the trocar has a lumen suitable for the guidewire 140) and the trocar, together with the cannula, is advanced up to the posterior atrial wall, as illustrated in FIG. 3. The trocar is then used for puncturing the atrial wall so that it, together with the inlet 104 of the cannula 100, is advanced into the atrium. Then the suture ring 122 is sutured securely to the posterior atrial wall and, once the suture ring 122 is securely joined to the posterior atrial wall, the trocar 130 may be withdrawn from the lumen 111 of the cannula 100, and the outlet 112 of the cannula 100 may be connected to the heart pump system. Retraction sutures may be used during the suturing and the suture ring is then designed for this.

The diameter $d_t$ of the trocar 130 equals the diameter of the lumen 111, so that the lumen 111 is closed in a fluid-tight manner. In particular, no fluid may penetrate through the lumen 111 through the drain element opening 110 to the proximal opening 114, either, for as long as the trocar is arranged in the lumen of the cannula 100.

Figure 4:
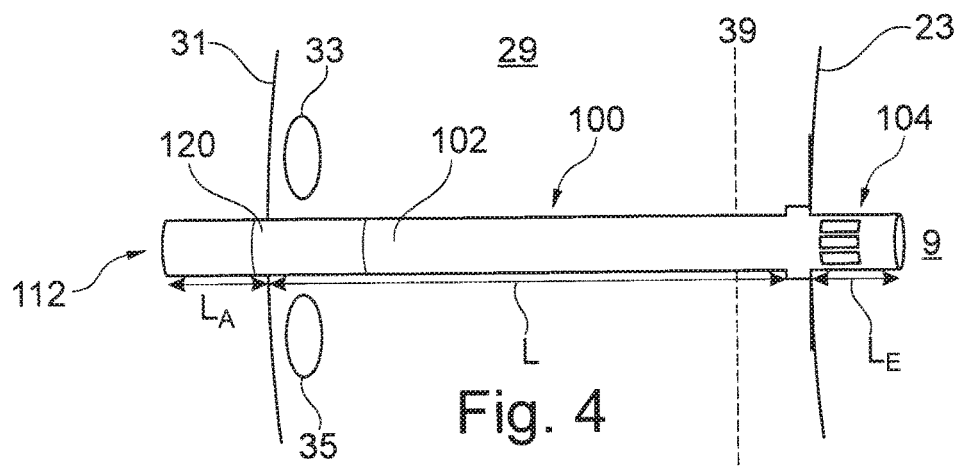
FIG. 4 is a schematic view of an implanted cannula.

FIG. 4 schematically depicts how an implanted cannula 100 is positioned in the body. The cannula 100 corresponds, for instance, to one of the cannulas depicted in FIGS. 2 and 3. The inlet 104 projects into the left atrium 9, the suture ring 122 being sutured to the posterior atrial wall 23. Alternatively, or in addition, the suture ring may be glued to the atrial wall. The cannula shaft 102 extends across the length L from the posterior atrial wall 23 through the interstitial space 29, through the intercostal space between the ribs 33 and 35, and through the skin 31. The web 120 is arranged on the cannula shaft such that the former is positioned in the region of the puncture 37 through the skin 31 and thus promotes growing into the skin 31 so that the risk of infection is minimized for the patient. The length $L_A$ of this part of the cannula shaft 102 is positioned outside of the body. The outlet 112 is again connected to a heart pump, for example. The length $L_A$ may be between 20 and 80 cm, for example. In other alternatives, lengths even greater than 80 cm are possible, for example 140 cm. The body axis 39 was drawn in to provide better orientation with respect to guiding the cannula 100. This is intended to clarify that the cannula is guided from the posterior atrial wall 23 through the left rib cage (as seen from a ventral view).

Although to this point it has merely been described that the inlet, in particular its distal opening, is positioned in the atrium, the length $L_E$ may also be selected such that the distal opening is positioned in the left ventricle. If there is a drain element, the drain element openings may be arranged such that when the cannula is implanted they are positioned either in the ventricle or in the atrium. The distances between the distal opening and the drain element are then appropriately coordinated. In other exemplary embodiments, the cannula may exclusively comprise drain element openings instead of a distal opening.

Figure 5:
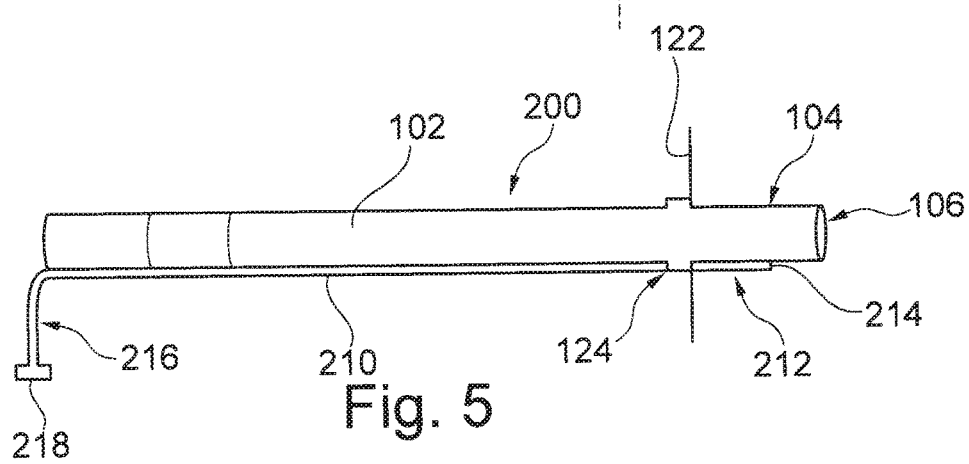
FIG. 5 depicts another embodiment of a cannula.
Figure 6:
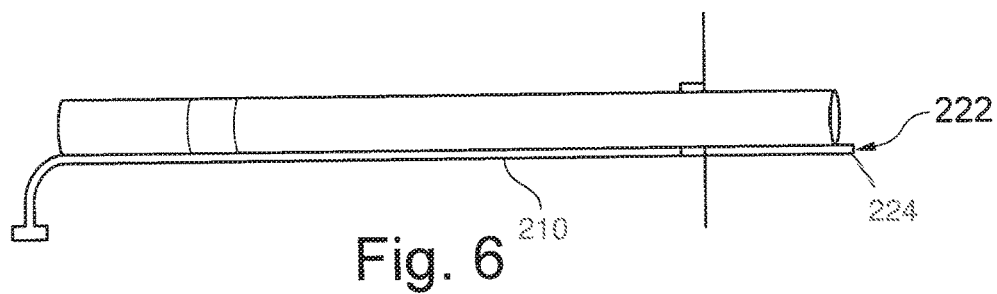
FIG. 6 depicts another embodiment of a cannula.

Another variant of a cannula shall be described using FIG. 5. The cannula 200 depicted in FIG. 5 essentially comprises all of the features of the cannula 100, but additionally also comprises a pressure sensing line 210 that extends along the cannula shaft 102. The pressure sensing line 210 has a pressure sensing line inlet 212 with a distal opening 214 that is positioned proximal to the distal opening 106, but distal to the distal end of a drain element opening 110. The pressure sensing line outlet 216 is positioned proximal to the proximal opening 114 of the cannula 200 and comprises an adapter 218 that is embodied for connecting to an external pressure measuring system. For instance, the connector may be a snap-fit connector or a luer lock for connecting to an external pressure measuring system. Such adapters have been known in the prior art for quite some time. The pressure in the atrium may be measured at any time by means of the pressure sensing line 210, which is integrated into the cannula 200. In this way it is not necessary to thread an additional pressure sensing line into the cannula itself, which must be accomplished at regular or irregular intervals in order to determine the pressures in the atrium. In the example in FIG. 5, the pressure sensing line 210 runs outside the cannula shaft 102 and is attached thereto in a material fit. The pressure sensing line 210 may either be glued or welded to the outer wall of the cannula shaft 102. The pressure sensing line 210 is guided through an opening 124 or a cut-out in the suture ring 122 so that it is assured that the pressure sensing line inlet 212 is positioned inside the atrium. Although in the present exemplary embodiment the distal opening 214 of the pressure sensing line inlet 212 is disposed proximal to the distal opening 106, as FIG. 6 illustrates, in another exemplary embodiment a distal opening 224 of a pressure sensing line inlet 222 may be disposed distal to the distal opening 106 of the cannula 100. In other exemplary embodiments, the distal opening of the pressure sensing line inlet may be flush with the distal opening 106 of the cannula 100.

Figure 7A:
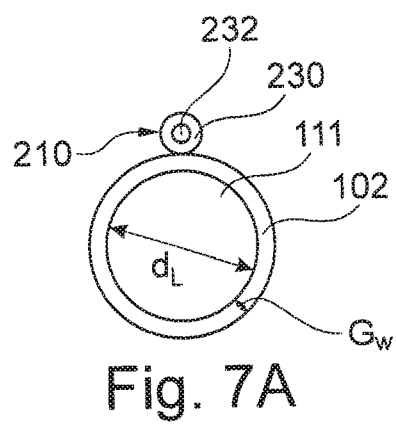
FIG. 7a depicts a first embodiment of an arrangement of a pressure sensing line.
Figure 7B:
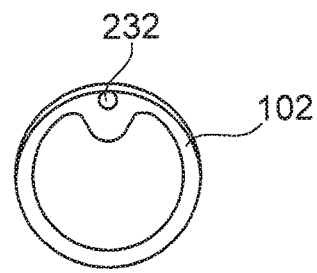
FIG. 7b depicts a second embodiment of an arrangement of a pressure sensing line.
Figure 7C:
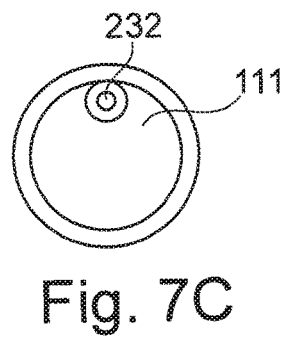
FIG. 7c depicts a third embodiment of an arrangement of a pressure sensing line.

The various positionings of the pressure sensing line in the cross-section shall be illustrated using FIGS. 7A through 7C. FIG. 7A depicts the wall of the cannula shaft 102 having the wall thickness $G_w$. The wall thickness is preferably constant and is between 1 and 5 mm. The lumen 111 of the cannula 100 has a diameter $D_L$ of 0.3 to 2 cm. The pressure sensing line 210 is arranged outside of the lumen 111 and has a separate line wall 230. The line wall may have a preferably constant wall thickness between 0.5 to 3 mm. The fluid, in this example, blood, may enter the lumen 232 through the distal opening, travel to the adapter, and thus be supplied for a pressure measurement by means of a pressure gauge in the external pressure measuring system. Alternatively, a pressure gauge may be arranged inside the pressure sensing line. This may be, for example, a membrane arranged in the pressure sensing line 210, wherein the force acting on the membrane may be converted to a pressure. To this end, the deflection or the force acting on the membrane must be forwarded to an external evaluation system. Forwarding may be accomplished, for instance, by means of an electrical line that runs inside the wall 230. However, to assure good flexibility, the actual pressure measurement will often take place in external pressure measuring systems.

In FIG. 7B, the lumen 232 is integrated into the wall of the cannula shaft 102. In FIG. 7C, the pressure sensing line is separate (similar to FIG. 7A); that is, it is not arranged in the wall of the cannula shaft 102, but runs inside the lumen 111. In this case, as well, the pressure sensing line may be joined to the wall of the cannula shaft 102 in a material fit.

Figure 8:
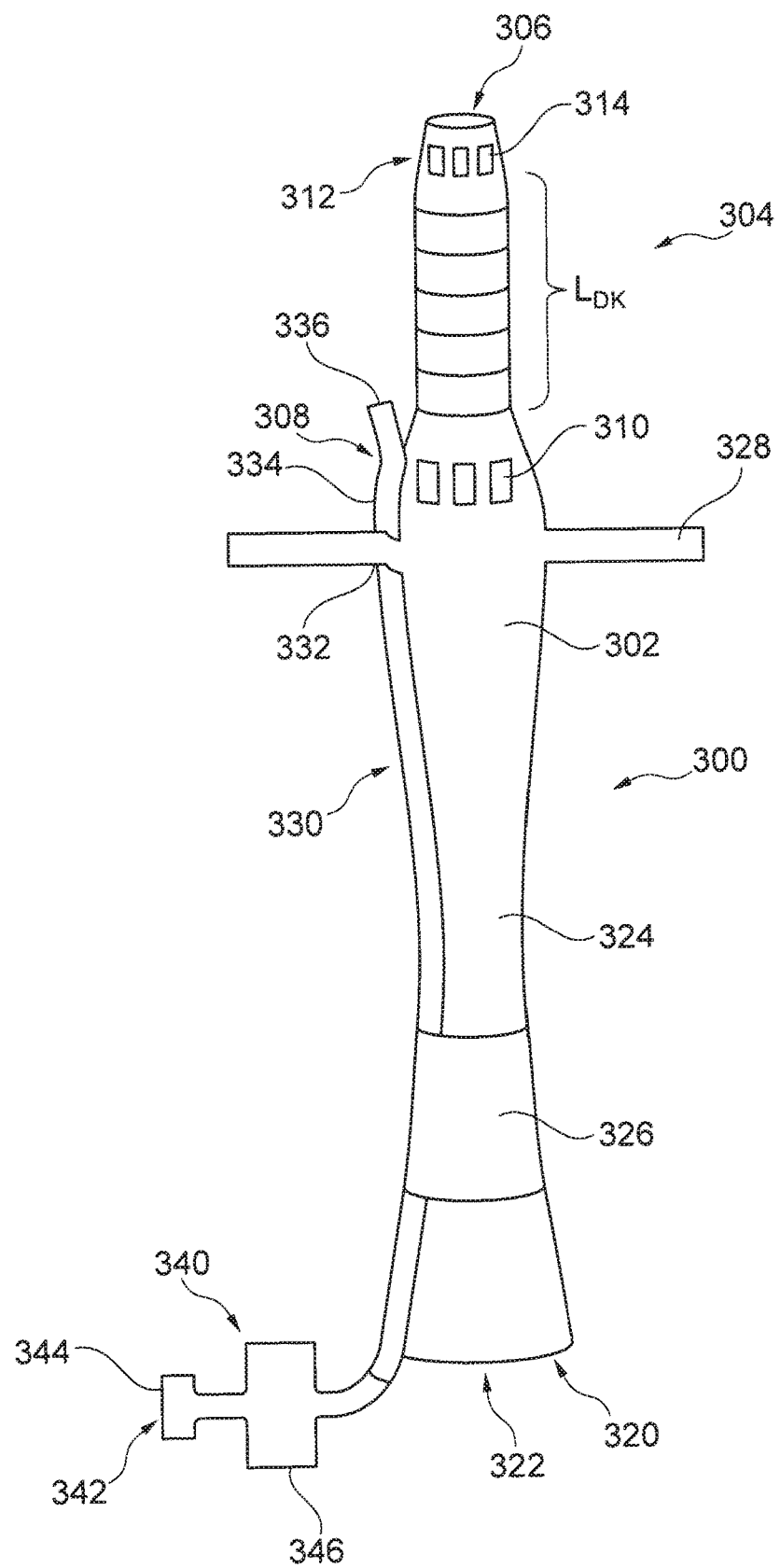
FIG. 8 depicts another embodiment of a cannula.

Another embodiment of a cannula for relieving the heart shall be explained using FIG. 8. The cannula 300 comprises (like the cannula 100) a cannula shaft 302 that is made of silicone. The cannula furthermore comprises an inlet 304 that, in addition to the distal opening 306, comprises a first drain element 308 having a plurality of openings 310 and a second drain element 312 that is positioned distal to the first drain element 308 and that has a plurality of openings 314. The first drain element 308 and the second drain element 312 are separated from one another by a distance $L_{dk}$. This length $L_{dk}$ is selected such that the first drain element is disposed in the atrium, while the second drain element 312 and the distal opening 306 extend through the mitral vale into the left ventricle. This has the advantage that blood may be drawn into the lumen of the cannula shaft 302 from the ventricle and furthermore blood may also be drawn through the openings 310 out of the atrium into the cannula shaft.

Optionally, contrasting strips 316 that are arranged transverse to the longitudinal axis of the cannula shaft are disposed between the first and second drain elements 308 and 312. The contrasting strips 316 represent an alternative to the contrasting strips 123 described for FIG. 2. In addition, the contrasting strips may comprise wire and thus impart additional stability to the region between the first and second drain elements. Alternatively, the strips may only provide stabilization for the cannula.

The proximal opening 322 of the outlet 320 is disposed opposite the distal opening 306. The lumen 324, which is furthermore accessible via the openings 314 and 310, extends between the proximal opening 322 and the distal opening 306.

The cannula 300 furthermore comprises a felt layer 326 that extends across a region of approx. 10 cm, preferably less than 10 cm but more than 5 cm. The felt 326 serves the same purpose as the web 120 in FIG. 2. In particular, this means that the length of the cannula shaft between the suture ring 328 and the felt 326 is dimensioned such that it reaches from the posterior atrial wall to the skin in the region of the skin puncture. Again, the cannula shaft extends for example between 50 and 80 cm from the felt 326 to the outlet 320, the outlet 320 being connected to a heart pump system.

The cannula 300 may optionally comprise a pressure sensing line 330 as has already been explained, for example, using FIGS. 5 through 7. The pressure sensing line 330 is designed such that it reaches through an opening 332 in the suture ring and there forms an inlet 334. The inlet has a distal opening 336 that is positioned distal to the distal end of the openings 310. The pressure sensing line is designed such that it can measure the pressure in the atrium. At its proximal end is disposed an outlet 340 that comprises an adapter 342 that has a proximal opening 344 and that may be connected, for example, to an external pressure measuring system. In addition, the pressure sensing line 330 has a pressure sensor 346 with its own evaluation device so that the atrial pressure may be measured via an external pressure measuring system, but also by the intrinsic pressure sensor 346.

Figure 8A:
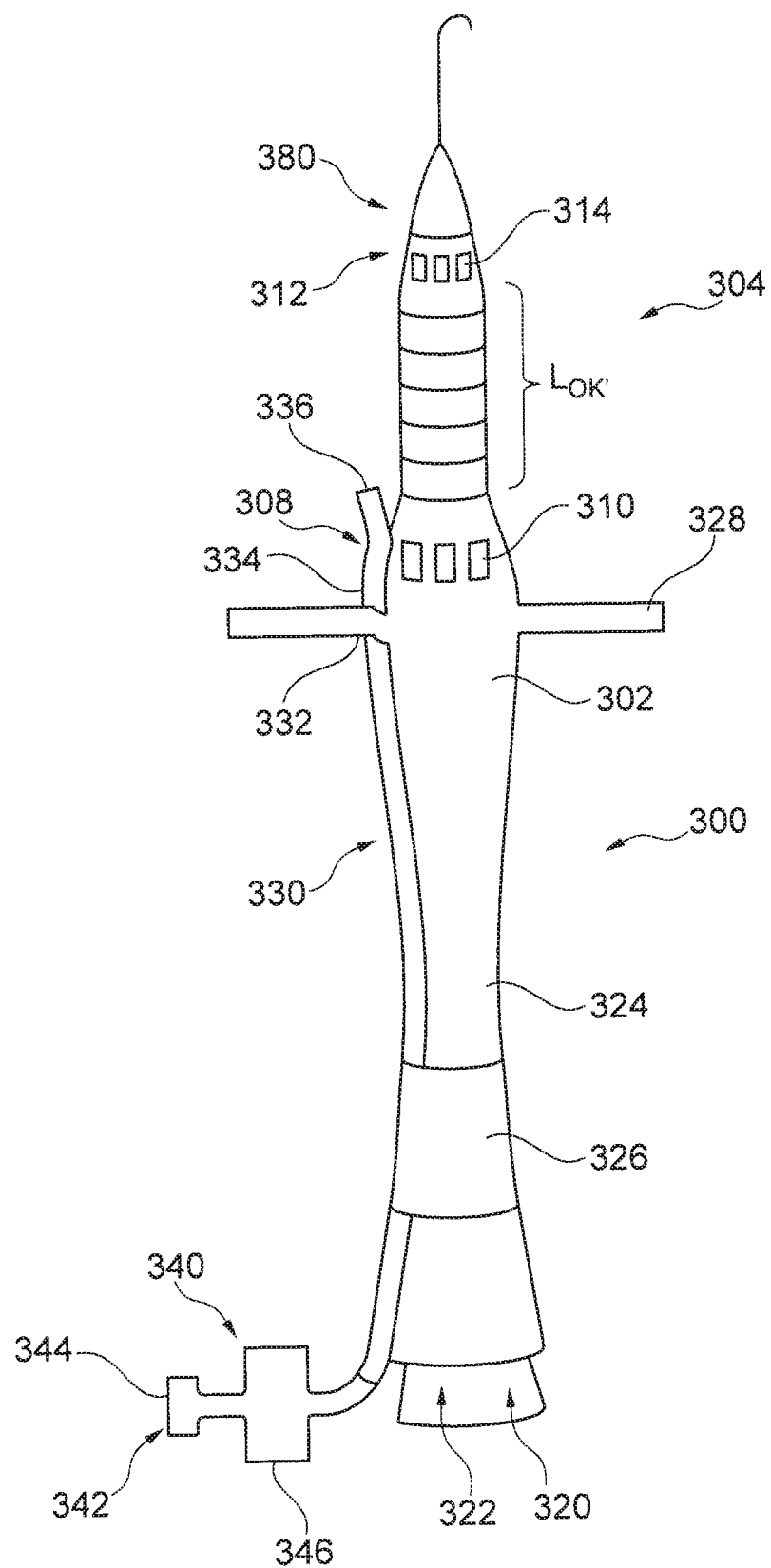
FIG. 8A depicts the embodiment from FIG. 8 with an inserted trocar.

FIG. 8A depicts the cannula 300 with an inserted trocar 380. This trocar is functionally comparable to the trocars in FIGS. 3 and 3A, i.e. it blocks the lumen 324 such that no fluid can travel to the outlet 320 through the inlet 306 nor through the drain element openings of the first drain element or of the second drain element as long as the trocar is inserted in the lumen 324. In this way the cannula system formed in this manner is suitable for being implanted "off-pump." To implant the cannula system in FIG. 8A using the Seldinger technique, it may furthermore be provided that the trocar has a lumen into which a guide wire may be threaded. In this application, this lumen is essentially equal to the diameter of the guide wire.

Figure 9:
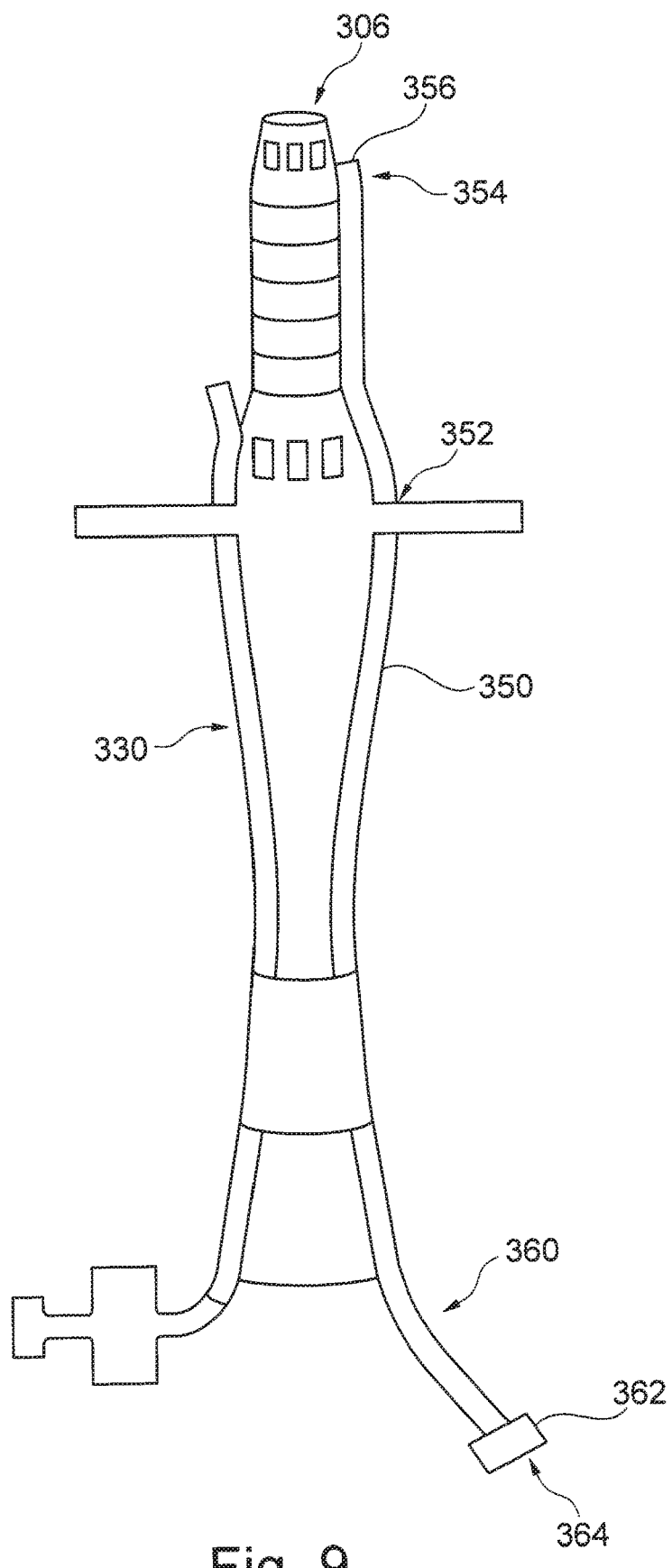
FIG. 9 depicts another embodiment of a cannula.

In another alternative, as depicted in FIG. 9, the cannula 300 comprises a second pressure sensing line 350. The latter may be present optionally or as an alternative to the pressure sensing line 330. The second pressure sensing line 350 is guided through an additional opening 352 through the suture ring and the distal opening 356 of its inlet 354 is positioned proximal to the proximal end of the openings of the second drain element 312. However, the distal opening 356 is arranged such that it is also positioned inside the ventricle. The second pressure sensing line 350 furthermore has an outlet 360 with an adapter 362 that, via its proximal opening 364, can connect the second pressure sensing line 350 to an external pressure measuring system. Since the second pressure sensing line terminates in the ventricle, the pressure in the ventricle may be measured at any time and without further surgical intervention.

Figure 10:
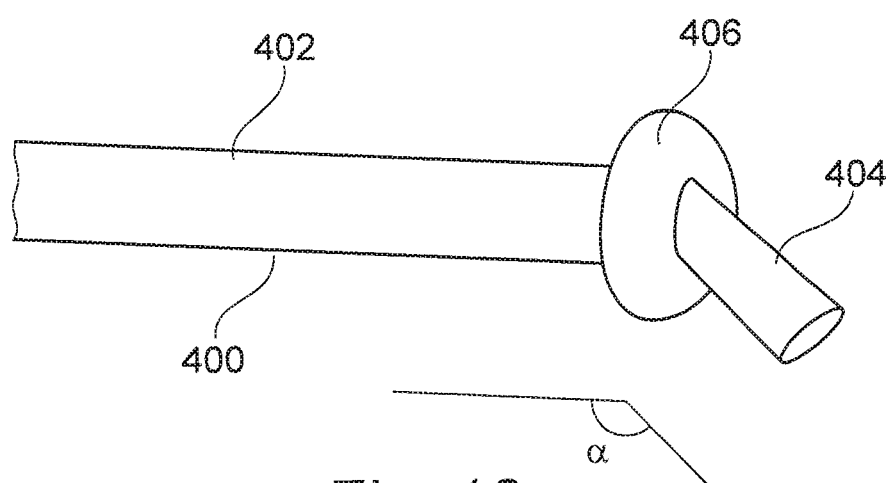
FIG. 10 depicts another embodiment of a cannula.

In an alternative embodiment, the previously depicted embodiments of the cannula may have an angle between the inlet and the remaining cannula shaft. This is illustrated in FIG. 10. The cannula 400 comprises a cannula shaft 402, an inlet 404, and a suture ring 406. A bend about an angle α, which may be between 30° and 75°, is located between the inlet 404 and the shaft 402. In the region of the bend is preferably arranged proximal to the suture ring 406 and contributes to the shape of the cannula, i.e., the cannula has this bend without the action of other forces. By inserting a trocar, for example the trocar as illustrated in FIG. 3, the bend may be straightened to an angle of less than 5°, which can facilitate insertion of the cannula into the body up to the posterior atrial wall. In other alternatives, the trocar may also be embodied such that it may initially be inserted straight so that the cannula 400 is extended, but the trocar, upon reaching the posterior atrial wall, is bent about the angle α using a wire mechanism, similar to a wire mechanism for a controllable catheter, and only then is the posterior atrial wall punctured by means of the trocar and only then is the inlet 404 inserted into the atrium. Such a trocar having a wire control for bending may be claimed independently of the cannulas described here.

Figure 11:
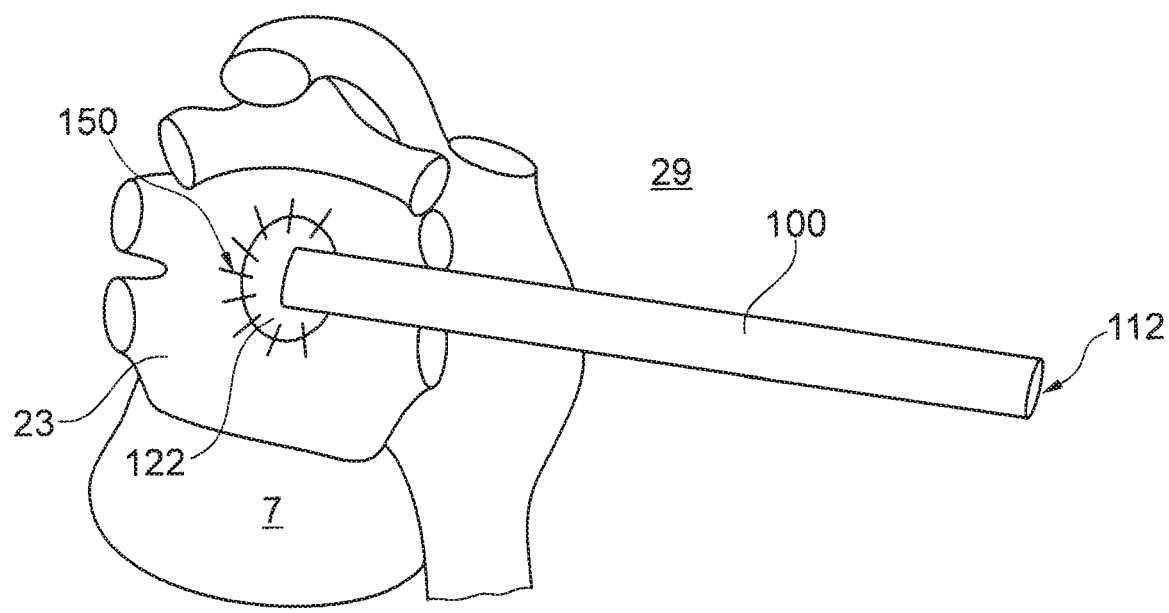
FIG. 11 is a schematic dorsal section through the rib cage of a human in which an implanted cannula is visible.
Figure 12:
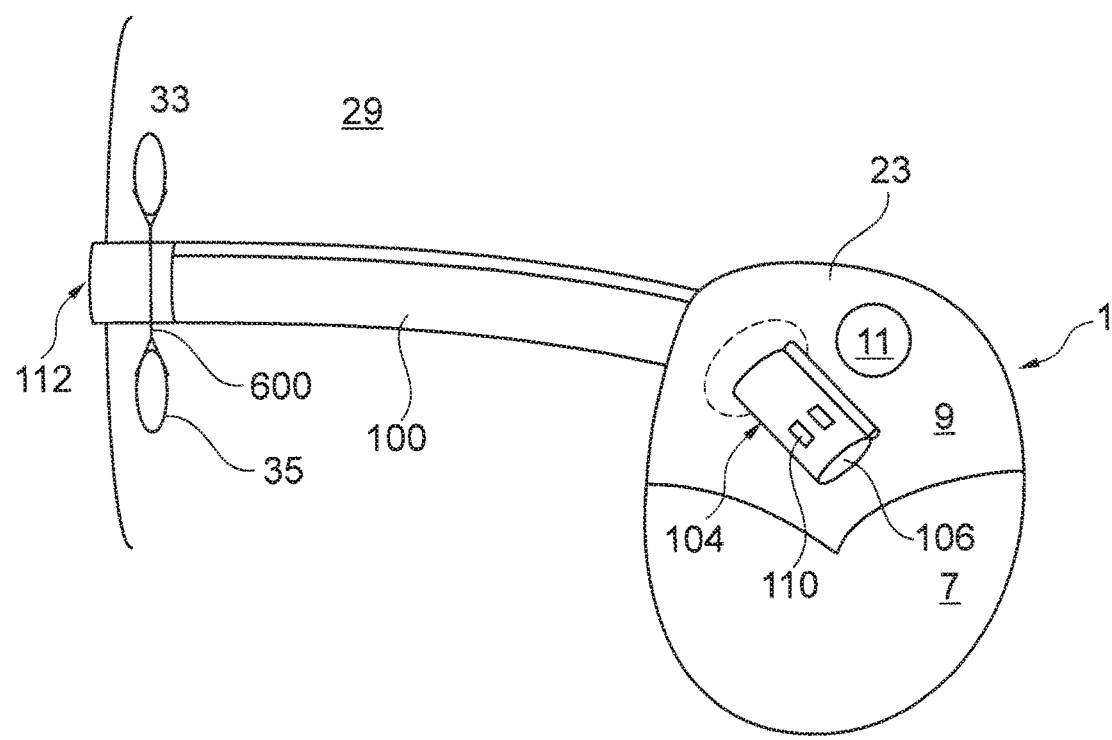
FIG. 12 is a schematic depiction of a ventral view of the segment depicted in FIG. 11.

FIG. 11 is a schematic dorsal section through the rib cage of a human, so that an implanted cannula 100 is visible. The cannula 100 extends from right to left through the interstitial space and is guided through an opening (not visible in this view) in the posterior atrial wall 23 into the left atrium (and, depending on the embodiment, into the ventricle). The suture ring 122 is joined by means of a suture or a plurality of sutures 150 to the posterior atrial wall. Viewing the segment depicted in FIG. 11 in a ventral view provides the situation depicted schematically in FIG. 12. It may clearly be seen that the cannula 100 was guided through the interstitial space 29 and through the posterior atrial wall 23 into the left atrium 9. In this way the inlet 104 extends into the atrium (or into the ventricle in other embodiments of the cannula). Blood may now be drawn out of the atrium (or ventricle) into a heart pump through the distal opening 106 and the drain elements 110 by means of the heart pump arranged at the outlet 112 and may then be supplied, for example to the subclavian blood vessel, through a pump outlet or a cannula connected to the pump outlet. To avoid closure of the cannula 100 in the intercostal space between the ribs 33 and 35, a corresponding spacer, for instance made of metal or plastic, may be inserted between the two ribs. This spacer 600 prevents the two ribs 33 and 35 from being pressed towards one another such that the lumen 111 of the cannula 100 is blocked such that blood can no longer be conveyed through the cannula 100.

Figure 13:
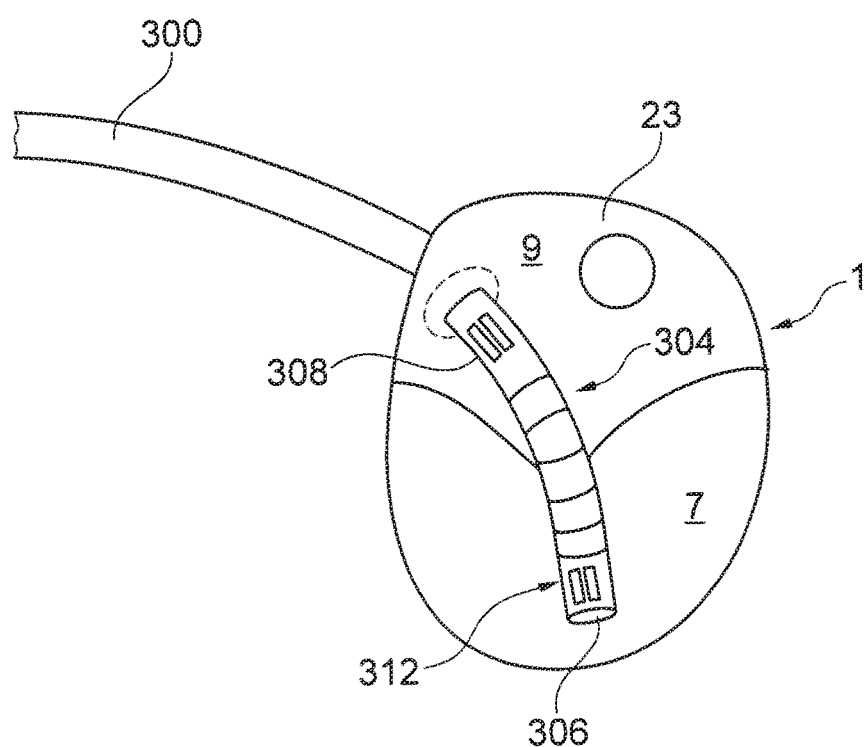
FIG. 13 depicts the situation following implantation of a cannula.

FIG. 13 depicts the situation following implantation of a cannula 300. The inlet 304 leads from the posterior atrial wall 23 into the left atrium 9 and the left ventricle 7. The distal opening 306, and the second drain element 312, remain inside the ventricle and the first drain element 308 remains inside the atrium. In this way blood may be suctioned by a pump arranged at the outlet of the cannula 300 out of the atrium and also out of the ventricle and supplied to the subclavian artery, for example via another cannula. Although not depicted in FIGS. 12 and 13, pressure sensing lines may optionally be part of the cannula as in the previous figures.

Figure 14:
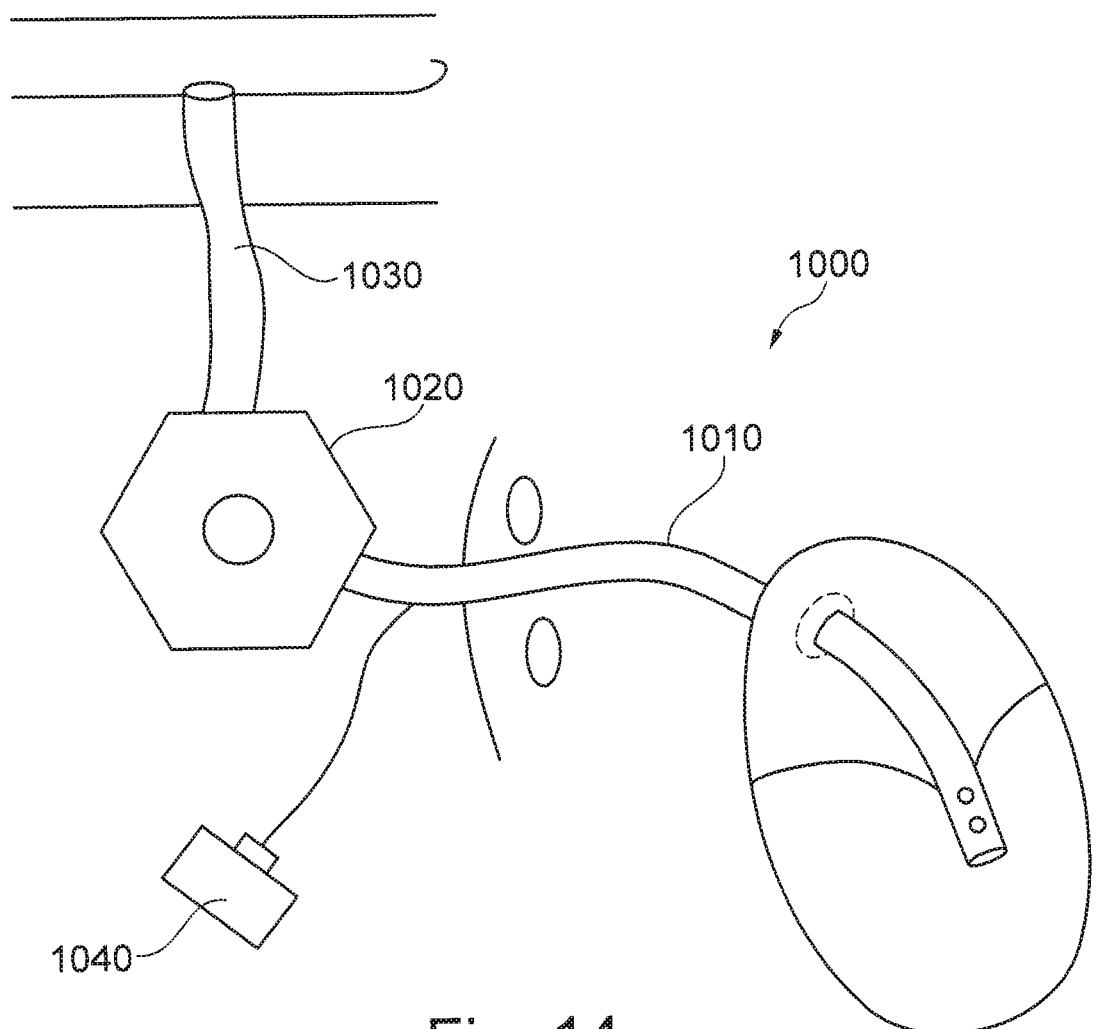
FIG. 14 is an exemplary depiction of a heart pump system.

Using FIG. 14 it shall briefly be described how a heart pump system according to the application may be configured with one of the previously described cannulas. The system 1000 depicted in FIG. 14 comprises, in addition to a cannula 1010, which may be provided for example by one of the cannulas described in FIGS. 2 through 13 or another cannula resulting from the embodiments of this application, a blood pump 1020 that embodies, for instance, a heart pump for an ECMO, ECLS, or other heart support. The heart pump is arranged outside of the human body and is connected to the outlet of the cannula 1010. The heart pump 1020 may also be a short-term pump that may be used only for a few days or months in a human according to regulatory requirements. If there is an extended need for heart supporting pumping, this pump may be replaced simply, without it being necessary for the patient to undergo further surgery. Pumps that may be used in the heart pump system are, for example, Centrimag® or Pedimag® from Thoratec, Rotaflow® or Rotassist® from Maquet, DP3 from Medos, Revolution® from Sorin, Biomedicus® from Medtronic, or similar pumps available on the market.

The output of the pump may be connected via an additional cannula to a subclavian blood vessel of the person, for example, so that the blood pump with the cannulas 1010 and 1030 forms a closed circuit. A pressure sensing line for the cannula 1010 may be connected to an external pressure measuring system 1040 via an appropriate adapter. External pressure measuring systems are known and sufficiently available in the clinical field. Thus the arterial or ventricular pressure may be seen via a display on the pressure sensing device 1040 at any time while the patient is undergoing care with the heart support system 1000.

The invention claimed is:

1. A cannula system comprising:
   a cannula including a cannula shaft having a heart-side inlet and a pump-side outlet and having a lumen extending between the inlet and the outlet, wherein a suture ring for joining the cannula to a left atrium is arranged on an exterior of the cannula shaft, and the outlet is configured to be connectable to a pump and the length of the cannula shaft between the suture ring and the outlet is such that the cannula shaft may be guided outward through an intercostal space, wherein, between the suture ring and the inlet, a first drain element and a second drain element are arranged on the cannula shaft and spaced apart from one another such that the first drain element is positioned in a left atrium and the second drain element is positioned in a left ventricle, the first drain element and the second drain element configured to drain into the same lumen that extends between the inlet and the outlet; and
   an obturator or a trocar blocking the lumen.

2. The cannula system of claim 1, wherein a distal end of the obturator or of the trocar projects out of the inlet of the cannula and the distal end is configured to puncture body tissue.

3. The cannula system of claim 1, wherein the obturator or the trocar has a guide lumen for accommodating a guidewire.

4. The cannula system of claim 1, wherein, between the suture ring and the inlet, the cannula shaft is long enough for the inlet to project through a left atrium into a left ventricle.

5. The cannula system of claim 1, wherein the inlet comprises at least one drain element.

6. The cannula system of claim 1, wherein a contrasting material is present between the suture ring and the inlet.

7. The cannula system of claim 1 further comprising a pressure sensing line having an inlet and an outlet, the inlet of the pressure sensing line arranged on a heart-side of the suture ring.

8. The cannula system of claim 7, wherein the pressure sensing line is guided along the exterior of the cannula shaft.

9. The cannula system of claim 7, wherein the pressure sensing line is guided in the lumen.

10. The cannula system of claim 7, wherein the outlet of the pressure sensing line is configured such that it may be coupled to an external pressure measuring system.

11. The cannula system of claim 1, wherein the cannula shaft has a length of more than 20 cm.

12. The cannula system of claim 1, wherein the cannula shaft has a wall thickness between 1 mm and 5 mm.

13. The cannula system of claim 1, wherein the cannula shaft is made of a biocompatible material.

14. The cannula system of claim 1, further comprising a pressure gauge.

15. The cannula system of claim 1, wherein the lumen is fluidly coupled to the first drain element and the second drain element.

* * * * *